United States Patent [19]

Winzenburg et al.

[11] Patent Number: 4,490,545
[45] Date of Patent: Dec. 25, 1984

[54] CYCLIC DIANHYDRIDES PREPARED FROM MALEIC ANHYDRIDE

[75] Inventors: Mark L. Winzenburg, Naperville; Ellis K. Fields, River Forest; Benjamin L. Shneider, Glen Ellyn, all of Ill.

[73] Assignee: Standard Oil Company (Indiana), Chicago, Ill.

[21] Appl. No.: 524,937

[22] Filed: Aug. 22, 1983

[51] Int. Cl.$^3$ .............................. C07D 307/93
[52] U.S. Cl. .................. 549/234; 204/158 HE; 528/353; 549/236; 549/241
[58] Field of Search ............ 549/234, 236, 241; 204/158 HE

[56] References Cited

U.S. PATENT DOCUMENTS 3,472,749 10/1969 Bradshaw ................. 549/234 X
4,360,657 11/1982 Nimry et al. ............. 549/234 X
4,371,701 2/1983 Fields et al. ............. 549/236 X

*Primary Examiner*—Richard L. Raymond
*Attorney, Agent, or Firm*—William C. Clarke; William H. Magidson; William T. McClain

[57] ABSTRACT

Cyclic dianhydrides and polyimides are prepared from maleic anhydride compounds and diolefins. The diolefins are alpha-, omega-linear diolefins of up to 100 carbon atoms or cyclic diolefins of up to 40 carbon atoms. The polyimides and copolyimides prepared from these cyclic dianhydrides are useful in films, fibers and coatings.

19 Claims, No Drawings

CYCLIC DIANHYDRIDES PREPARED FROM MALEIC ANHYDRIDE

FIELD OF THE INVENTION

This invention relates to cycloaliphatic tetracarboxylic acid dianhydrides of the structures

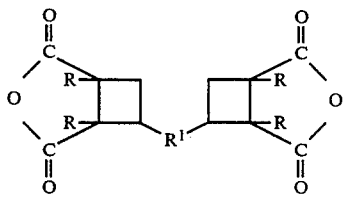

and

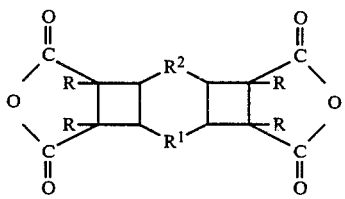

wherein R is selected from the group consisting of alkyl groups of 1 to 10 carbon atoms and alkylene groups of from 2 to 20 carbon atoms linked together to form a ring, and $R^1$ and $R^2$ are individually selected from the group consisting of alkylene groups of from 1 to 10 carbon atoms and aralkylene groups of from 8 to 20 carbon atoms with the provision that hydrocarbon moieties of said groups can contain stable linkages selected from the group consisting of —O—,

—SO—, —SO$_2$—, and —S— radicals.

This invention also relates to novel polyimides and copolyimides prepared from these novel cyclic dianhydrides.

BACKGROUND OF THE INVENTION

It is known to make dianhydrides from maleic anhydride as is taught in commonly-assigned Ser. No. 294,322, and Ser. No. 386,891, which are hereby incorporated by reference. It is also known to make polyimides from dianhydrides and aromatic amines. This is disclosed in U.S. Pat. No. 3,179,634 (1965). British Patent Specification No. 570,858 discloses various processes for making fiber-forming polymers.

In reviewing these references, it is clear that the reaction of anhydrides prepared from maleic anhydride compounds with olefins in a mole ratio of 2:1, two moles of anhydride to one mole of olefin, to prepare dianhydrides has not been contemplated in the prior art. Also, the prior art has not contemplated the novel dianhydrides prepared by photocycloaddition of maleic anhydride compounds to at least one cyclic diolefin of the structural formula

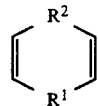

wherein $R^1$ and $R^2$ are individually selected from the group consisting of alkylene moieties of from 1 to 10 carbon atoms and aralkylene moieties of from 8 to 20 carbon atoms or alpha, omega-diolefins of the structure (CH$_2$=CH$_2$CH$_2$)$_2$R' wherein R' is selected from the group consisting of alkylene groups of from 0 to 20 carbon atoms, aralkylene groups of from 8 to 20 carbon atoms and aryl groups of 6 to 20 carbon atoms with the provision that hydrocarbon linkages of said moieties can contain stable linkages selected from the group consisting of —O—,

—SO—, SO$_2$ and —S— radicals. The maleic anhydride compound is selected from the group consisting of maleic anhydride compounds of the structural formula

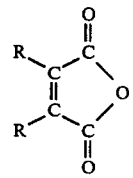

wherein R is individually selected from the group consisting of alkyl moieties of from 1 to 10 carbon atoms and alkylene moieties of from 2 to 20 carbon atoms linked together to form a ring. Examples are dimethyl maleic anhydride and 1-cyclohexene-1,2-dicarboxylic acid anhydride, a compound made by isomerizing the Diels-Alder adduct of butadiene and maleic anhydride (M. E. Bailey and E. D. Amstutz, JACS, 78, 3828 (1956)).

The general object of this invention is to provide novel dianhydrides prepared from maleic anhydride compounds with diolefins in a mole ratio of 2:1 and to provide novel polyimides based on these novel dianhydrides. A more specific object of this invention is to provide novel dianhydrides from dimethyl maleic anhydride designated as compound (1), or 1-cyclohexene-1,2-dicarboxylic anhydride, designated as compound (2) and diolefins selected from the group consisting of 1,5-cyclooctadiene, 1,5-hexadiene, and 1,7-octadiene. Another more specific object of this invention is also to provide novel polyimides prepared from the said novel dianhydrides. Another specific object of this invention is to provide a simple procedure for the preparation of these dianhydrides by the photocycloaddition of the maleic anhydride compounds to the respective diolefins.

SUMMARY OF THE INVENTION

This invention relates to cyclic dianhydrides prepared from maleic anhydride compounds and maleic anhydride condensation products with diolefins in mole ratios of 2:1 by photocycloaddition in the presence of actinic energy and a U.V. light sensitizer.

This invention further relates to cycloaliphatic tetracarboxylic acid anhydrides of the structures

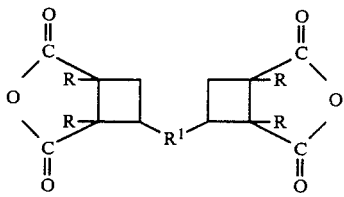

and

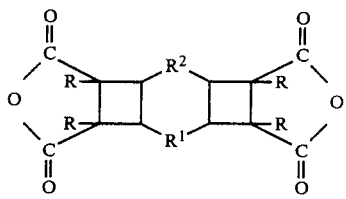

wherein R is selected from the group consisting of alkyl groups of 1 to 10 carbon atoms and alkylene groups of from 2 to 20 carbon atoms linked together to form a ring, and $R^1$ and $R^2$ are individually selected from the group consisting of alkylene groups of from 1 to 10 carbon atoms and aralkylene groups of from 8 to 20 carbon atoms with the provision that hydrocarbon moieties of said groups can contain stable linkages selected from the group consisting of —O—,

—SO—, —SO$_2$—, and —S— radicals. The cyclic dianhydrides are useful in the preparation of novel polyimides and copolyimides.

DETAILS OF THE INVENTION

This invention relates to cycloaliphatic tetracarboxylic acid anhydrides prepared from maleic anhydride compounds of this invention by the photocycloaddition of maleic anhydride compounds to alpha-, omega-linear diolefins of from 4 to 100 carbon atoms and cyclic diolefins of the structural formula

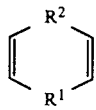

wherein $R^1$ and $R^2$ are individually selected from the group consisting of alkylene moieties of from 1 to 10 carbon atoms and aralkylene moieties of from 8 to 20 carbon atoms with the provision that hydrocarbon moieties of said linear diolefins, alkylene groups and aralkylene groups can contain stable linkages selected from the group consisting of —O—,

—SO—, —SO$_2$—, and —S— radicals.

This invention further relates to cycloaliphatic tetracarboxylic acid anhydrides of the structures

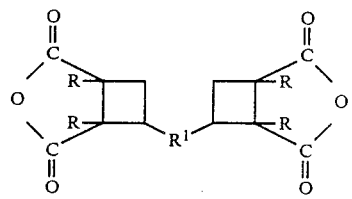

and

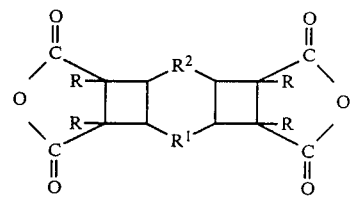

wherein R is selected from the group consisting of alkyl groups of 1 to 10 carbon atoms and alkylene groups of from 2 to 20 carbon atoms linked together to form a ring, and $R^1$ and $R^2$ are individually selected from the group consisting of alkylene groups of from 1 to 10 carbon atoms and aralkylene groups of from 8 to 20 carbon atoms with the provision that hydrocarbon moieties of said groups can contain stable linkages selected from the group consisting of —O—,

—SO—, —SO$_2$—, and —S— radicals.

The photocycloaddition products can be prepared by reacting dimethyl maleic anhydride (1) or 1-cyclohexene-1,2-dicarboxylic anhydride (2) with a diolefin in the presence of a U.V. light sensitizer using actinic radiation as an energy source at a temperature from $-10°$ C. to about 150° C.

The 1-cyclohexene-1,2-dicarboxylic anhydride (2) is prepared according to the method of Bailey, op. cit., by isomerizing the Diels-Alder adduct of butadiene and maleic anhydride with a few wt% of P$_2$O$_5$.

The diolefins can be cyclic, (CH$_2$=CH$_2$CH$_2$)$_2$ or (CH$_2$=CH$_2$CH$_2$)$_2$R' wherein R' is preferably from the group consisting of alkylene, aralkylene and arylene moieties of from 1 to 20 carbon atoms. Examples are 1,5-cyclooctadiene, 1,3-cyclooctadiene, 1,5-hexadiene, 1,6-heptadiene, 1,7-octadiene, etc., to 1,17-octadecadiene, 1,4-diallylbenzene, and 4,4'-(1,4-phenylene)bis(1-butene). The preferred diolefins are from 6 to 8 carbon atoms because they are cheap, reactive and readily available.

The molar ratios of the reactants to prepare the novel dianhydrides, i.e., the ratio of maleic anhydride derivative and the diolefin, is 2:1 to 10:1, preferably 2:1. A 2:1 ratio is required to obtain the resulting dianhydride. Use of a solvent, such as toluene, heptane, hexane, benzene, acetone, or dioxane at concentrations of 1 to 85 weight percent, is convenient. When water-miscible solvents, such as acetone or dioxane, are used, water up to 50% by weight of organic solvent may be incorporated. In such cases, or when water is used with immiscible solvents, such as heptane or benzene, up to 50% by weight, phase-transfer agents, such as cetyl trimethyl ammonium bromide, benzyl triethyl ammonium chloride, benzyl triphenyl phosphonium chloride, etc., are incorporated at concentrations of 0.001 to 1% by weight of total solvent.

Toluene is the preferred solvent. 25 to 85 weight percent is the preferred concentration range of the reactants.

It is essential that at least one U.V. light optically-active sensitizer be used in conjunction with the application of actinic radiation of wavelengths of approximately 250–400 nanometers, preferably from 300 to 370 nanometers in the ultra-violet light range. The term sensitizer can be defined as being an organic material which increases spectral response. Typical sensitizers are U.V. absorbers, such as benzophenone, acetophenone triphenylene, biphenyl and anthraquinone. Suitable U.V. sensitizers include benzophenone and acetophenone.

Benzophenone is the preferred U.V. sensitizer. Sufficient U.V. sensitizer is added to give final concentrations of 0.02 to 1% by weight in the total reaction mixture; 0.05 to 0.25% by weight is preferred. Alternatively, the sensitizer may be introduced bound to an ion-exchange resin in a relatively insoluble form.

The reaction may be run in any type of open or sealed vessel, suitably agitated.

The lamps used were a General Electric Sunlamp ™ and a Sylvania 15 watt black light Model F15T8/BLB. The G.E. Sunlamp ™ has 4.47 radiated watts in the ultraviolet range from 280 to 400 nanometers, and 7.03 radiated watts in the visible light range of 400 to 700 nanometers.

Workup generally consists of distilling off the solvent and crystallizing the photoadduct product from a suitable solvent.

The novel polyimides and copolyimides can be formed by reacting the novel dianhydrides with diamines or mixtures of diamines. The dianhydrides react readily with the diamine to form high molecular weight polyimides. In the novel process both aliphatic and aromatic diamines can be polymerized with the dianhydrides in a solution polymerization to form high molecular weight polyimides.

The process for the manufacture of the novel polyimides and copolyimides comprises reacting about equal molar amounts of the dianhydride with a primary diamine or a mixture of primary diamines. The molecular ratio of dianhydride to the primary diamine may be in the range of 1.2:1 to 1:1.2, preferably in the range of 1:1. In a suitable method, the reaction is conducted as a batch reaction at a temperature of about 130° C. to 300° C. for a period of about 2 to 8 hours in a nitrogen-containing organic polar solvent, such as N-methyl-2-pyrrolidinone, N,N-dimethylacetamide or pyridine. The dianhydride can be replaced partially by another aliphatic or aromatic dianhydride up to about 70 mole percent.

The other dianhydrides are characterized by the following formula:

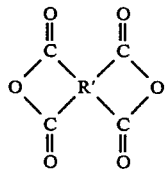

wherein R' is a tetravalent organic radical selected from the group consisting of aromatic, aliphatic, cycloaliphatic, heterocyclic, combination of aromatic and aliphatic, and substituted groups thereof. However, the preferred dianhydrides are those in which the R' groups have at least 6 carbon atoms wherein the 4 carbonyl groups of the dianhydride are each attached to separate carbon atoms and wherein each pair of carbonyl groups is directly attached to adjacent carbon atoms in the R' group to provide a 5-membered ring as follows:

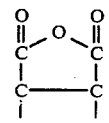

The preferred dianhydrides, as recited above, yield, upon reaction with the diamines, polyimides having outstanding physical properties. Illustrations of other dianhydrides suitable for use in the present invention include: pyromellitic dianhydride; 2,3,6,7-naphthalene tetracarboxylic dianhydride; 3,3',4,4'-diphenyl tetracarboxylic dianhydride; 1,2,5,6-naphthalene tetracarboxylic dianhydride; 1,2,3,4-cyclopentane tetracarboxylic dianhydride; 2,2',3,3'-diphenyl tetracarboxylic dianhydride; 2,2-bis(3,4-dicarboxyphenyl)propane dianhydride; 3,4-dicarboxylphenyl sulfone dianhydride; 2,3,4,5-pyrrolidone tetracarboxylic dianhydride; 3,4,9,10-perylene tetracarboxylic dianhydride bis(3,4-dicarboxyphenyl)ether dianhydride; 3,3',4,4'-benzophenonetetracarboxylic dianhydride; bis(3,4-dicarboxyphenyl)sulfide dianhydride; bis(3,4-dicarboxyphenyl)methane dianhydride; 1,4,5,8-naphthalenetetracarboxylic dianhydride; tricyclo[4,2,2,0$^{2,5}$]-dec-7-ene-3,4,9,10-tetracarboxylic dianhydride; 3,6-ethenohexahydropyromellitic dianhydride; cyclobutane-1,2,3,4-tetracarboxylic dianhydride; 1,3-dimethylcyclobutane-1,2,3,4-tetracarboxylic dianhydride; and 1,2,3,4-tetramethylcyclobutane-1,2,3,4-tetracarboxylic dianhydride. The polycondensation can also be carried out as a continuous process. The polycondensation can suitably be carried out at a temperature of 130° C. to 300° C., preferably at a temperature of 180° C. to 250° C. The novel polyimides of this invention can have the following recurring structure wherein R is selected from the group consisting of alkyl groups of 1 to 10 carbon atoms and alkylene groups of from 2 to 20 carbon atoms linked together to form a ring,

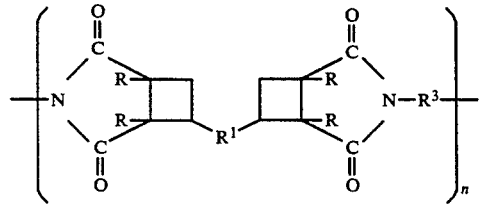

and

-continued

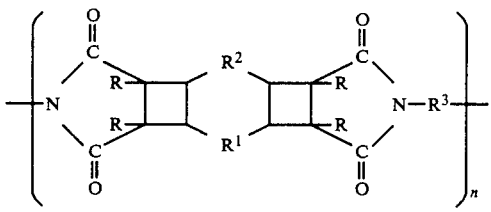

The radicals $R^1$ and $R^2$ are individually selected from the group consisting of alkylene groups of 1 to 10 carbon atoms and aralkylene groups of from 8 to 20 carbon atoms, with the provision that hydrocarbon moieties of said groups can contain stable linkages comprising —O—,

—SO—, —SO$_2$—, and —S— radicals. R is preferably methyl. $R^1$ and $R^2$ are preferably alkylene radicals of from 2 to 4 carbon atoms linked to the butane rings. $R^3$ is selected from the group consisting of alkylene groups of from 2 to 10 carbon atoms, arylene groups of 6 to 20 carbon atoms and aralkylene groups of from 8 to 20 carbon atoms, with the provision that hydrocarbon moieties of said groups can contain stable linkages selected from the group consisting of —O—,

—SO—, —SO$_2$—, and —S— radicals. The n is a whole number from 1 to 1000. The radical $R^3$ is derived from aliphatic, aromatic, araliphatic or cycloaliphatic diamines, such as ethylenediamine, propylenediamine, 2,2-dimethylpropylene diamine, tetramethylene diamine, hexamethylene diamine, octamethylene diamine, nonamethylene diamine, decamethylene diamine, dodecamethylene diamine, 4,4'-diaminodicyclohexylethane, xylylene diamine and bis(aminomethyl)cyclohexane. Suitable aromatic diamines useful in the process include para- and meta-phenylenediamine, 4,4'-oxydianiline, thiobis(aniline), sulfonylbis(aniline), diaminobenzophenone, methylenebis(aniline), benzidine, 1,5-diaminonaphthalene, oxybis(2-methylaniline), thiobis(2-methylaniline), and the like. Examples of other useful aromatic primary diamines are set out in U.S. Pat. No. 3,494,890 (1970) and U.S. Pat. No. 4,016,140 (1972) both incorporated herein by reference. The preferred diamines are 1,6-hexanediamine, 1,12-dodecanediamine and 4,4'-oxydianiline.

In some cases the polyimide may be further polymerized under "solid-state polymerization" conditions. The term solid-state polymerization refers to chain extension of polymer particles under conditions where the polymer particles retain their solid form and do not become a fluid mass. The solid-state polymerization can be carried out below the melting point of the polyimide and can be conducted in several ways. However, all techniques require heating the ground or pelletized polyimide below the melting point of the polyimide, generally at a temperature of about 175° C. to 300° C. while either sparging with an inert gas, such as nitrogen or operating under vacuum. In cases where the polyimides and copolyimides have a low melt temperature, they can be polymerized in the melt under vacuum in thin sections or using thin film reactors known in the art.

Injection molding of the novel polyimide is accompanied by injecting the polyimide into a mold maintanined at a temperature of about 25° C. to 150° C. In this process a 20 second to 1 minute cycle is used with a barrel temperature of about 125° C. to 350° C. The latter will vary depending on the $T_g$ of the polymer being molded.

The novel polyimides have excellent mechanical and thermal properties and can readily be molded into useful articles or formed into fibers, films, laminates or coatings.

Infrared spectra of the polyimides have confirmed the polyimide structure.

It has been found that the polyimides and copolyimides of this invention are improved by the addition of reinforcing material. Suitably about 25 to 60 percent by weight of glass fibers, glass beads or graphite or a mixture of these can be incorporated into the polyimides and copolyimides. Any standard commercial grade then can be used as reinforcing agents. Glass beads ranging from 5 mm to 50 mm in diameter may also be used as reinforcing material. Injection molding of the novel glass-filled polyimide is accomplished by injecting the polyimide into a mold maintained at a temperature of about 50° C. to 150° C. In this process a 25 to 28 second cycle is used with a barrel temperature of about 125° C. to 350° C. The injection molding conditions are given in Table I.

TABLE I

| Mold Temperature | 50° C. to 150° C. |
|---|---|
| Injection Pressure | 15,000 to 19,000 psi and held for 1 to 3 seconds |
| Back Pressure | 100 to 220 psi |
| Cycle Time | 25 to 28 seconds |
| Extruder: | |
| Nozzle Temperature | 125° C. to 350° C. |
| Barrels: | |
| Front heated to | 125° C. to 350° C. |
| Screw: | 20 to 25 revolutions/minute |

The following examples illustrate the preferred embodiment of the invention. It will be understood that the examples are for illustrative purposes only and do not purport to be wholly definitive with respect to conditions or scope of the invention.

EXAMPLE I

Preparation and characterization of 3,3'-(1,2-ethandiyl)bis(1,2-dimethylcyclobutane-1,2-dicarboxylic acid anhydride) (3) were as follows:

A one-liter Pyrex Erlenmeyer flask was charged with dimethyl maleic anhydride (1) (18.9 g, 0.15 mole), 1,5-hexadiene (6.16 g, 0.075 mole), benzophenone (1.0 g, 5.5 mmole), and toluene (100 ml). The flask was equipped with a water-cooled condenser and irradiated with a General Electric Sunlamp TM placed about four inches from the bottom of the flask. The reaction was kept under nitrogen during this time. After seven days, the resulting precipitate was collected on a filter, washed with toluene, and air dried. One recrystallization from acetone gave 18.9 g (75 mole %) of (3). Three additional recrystallizations from acetone gave 8.2 g of pure (3) mp 208° C. to 210° C. The structure of (3) below was confirmed by elemental microanalysis, infrared and $^{13}$C NMR spectroscopy, and mass spectrometry.

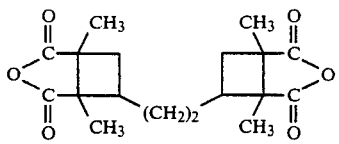
(3)

EXAMPLE II

Preparation and characterization of 3,3'-(1,4-butandiyl)bis(1,2-dimethylcyclobutane-1,2-dicarboxylic acid anhydride) (4) were as follows:

Compound (4) was prepared in the same manner as (3) employing (1) (12.6 g, 0.10 mole), 1,7-octadiene (2.76 g, 0.025 mole), benzophenone (1.0 g, 5.5 mmole), and toluene (100 ml). After 1 week of irradiation, 12.7 g of solids were isolated, a mixture of (4) and the photodimer of (1). From this, 4.0 g (22 mole %) of (4) were isolated as white crystals by recrystallization from acetone. Two more recrystallizations gave pure (4), mp 208° C. to 210° C. The structure was confirmed by elemental microanalysis, IR, and $^{13}C$ NMR and mass spectrometry.

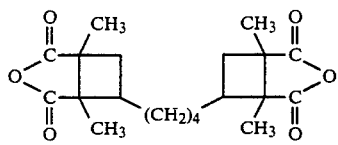
(4)

EXAMPLE III

Synthesis and characterization of tricyclo[10.2.0.0$^{4,7}$]dodecane-5,6,11,12-tetramethyl-5,6,11,12-tetracarboxylic acid, 5:6,11:12 dianhydride (5) were as follows:

In the procedure of Example I, a one-liter Pyrex Erlenmeyer flask was charged with (1) (76.5 g, 0.607 mole), 1,5-dyclooctadiene (32.8 g, 0.303 mole), benzophenone (5.0 g, 0.027 mole), and toluene (375 ml). The flask was fitted with a water-cooled condenser and irradiated with a General Electric Sunlamp TM placed about four inches from the bottom of the flask. The reaction was kept under an atmosphere of nitrogen during this time. After a total of nine days, the resulting precipitate was collected, washed with acetone, and air-dried to yield 76.5 g (70%) of (5). It was recrystallized from acetone to yield crystalline (5), mp. 360° C. to 365° C., with decomposition. The structure of (5) was characterized by carbon and hydrogen elemental analyses, and by infrared, proton and carbon-13 NMR, and mass spectrometry. All confirm the proposed formulation of (5) shown below. The multiplicity of $^{13}C$-NMR signals and the presence of two distinct methyl singlets in the $^1H$-NMR spectrum strongly suggest that (5) is a mixture of stereoisomers.

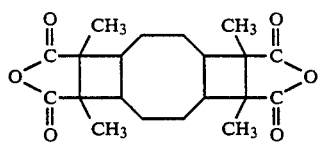
(5)

EXAMPLE IV

Preparation and characterization of 7,7'-(1,2-ethandiyl)bis(bicyclo[4.2.0]octane-1,6-dicarboxylic acid anhydride) (6) were as follows:

In the procedure of Example I, a one-liter Pyrex Erlenmeyer flask was charged with 1-cyclohexene-1,2-dicarboxylic acid anhydride (2) (15.2 g, 0.100 mole), 1,5-hexadiene (2.02 g, 0.0250 mole), benzophenone (1.0 g, 5.5 mmole), and toluene (200 ml). The flask was purged with nitrogen for twenty minutes and then fitted with a reflux condenser attached to a nitrogen supply and a bubbler. The flask was irradiated with a General Electric Sunlamp TM placed about four inches from the bottom of the flask. After seven days, irradiation was discontinued and the precipitated product was collected on a filter. The filtrates were concentrated by evaporation to yield more solid. The combined solids (4.8 g, 50 mole %) were recrystallized two times from acetone to yield 2.0 g (21 mole %) of (6) as a white crystalline solid, mp. 258° C. to 261° C. The structure of (6) below was confirmed by elemental microanalysis, IR, and mass spectrometry.

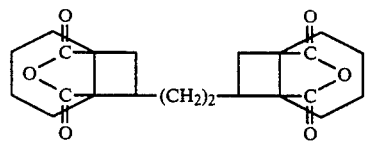
(6)

EXAMPLE V

Preparation and characterization of 7,7'-(1,4-butandiyl)bis(bicyclo[4.2.0]octane-1,6-dicarboxylic acid anhydride) (7) were as follows:

In the procedure of Example I, compound (7) was prepared in the same manner as (3) with (2) (15.2 g, 0.100 mole), 1,7-octadiene (2.76 g, 0.0250 mole), benzophenone (1.0 g, 5.5 mmole), and toluene (100 ml). 3.5 g (34 mole %) of crude (7) were isolated. Three recrystallizations from toluene gave 1.5 g (14.6 mole %) of (7) as white crystals, mp. 195° C. to 198° C. The structure of (7) below was confirmed by elemental microanalysis, IR and mass spectrometry.

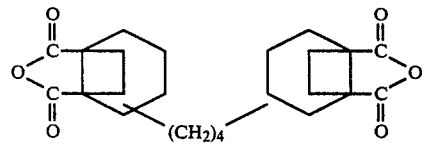
(7)

In a subsequent preparation of (7), a 26 mole % yield was obtained after two weeks of irradiation. Starting materials were still present in the reaction mixture. No further attempt of yield optimization was made.

EXAMPLE VI

Preparation and characterization of pentacyclo[16.4.0.0$^{2,15}$.0$^{5,12}$.0$^{6,11}$]eicosane-1,6,11,16-tetracarboxylic acid, 1:16,6:11-dianhydride (8) were as follows:

In the procedure of Example I, a one-liter Pyrex Erlenmeyer flask was charged with (2) (30.4 g, 0.2 mole), 1,5-cyclooctadiene (10.82 g, 0.1 mole), benzophenone (2.0 g, 0.01 mole), and toluene (200 ml). The flask was fitted with a water-cooled condenser and irradiated with a General Electric Sunlamp TM placed about four inches from the bottom of the flask. The reaction was kept under an atmosphere of nitrogen during this time. After five days the toluene was distilled from the reaction mixture. The residue was slurried in a little acetone, collected on a filter, and suction-dried to yield 18.0 g (44 mole %) of (8). Recrystallization from acetone gave flat white plates, mp. 248° C. to 250° C. The product (8) was characterized by elemental analysis for C and H, by infrared and carbon-13 NMR spectroscopy, and by mass spectrometry. The carbon-13 NMR spectrum of (8) showed that it was a mixture of stereoisomers of the structure below:

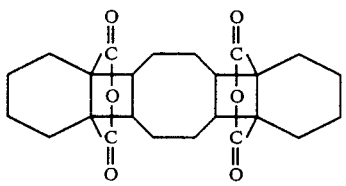
(8)

EXAMPLE VII

Preparation and characterization of polyimide poly(-dodecamethylene-3,3'-(1,2-ethandiyl)bis(1,2-dimethyl-cyclobutane-1,2-dicarboximide)) (9) were as follows:

A 100-ml, three-neck, round-bottom flask was equipped with a sitrring bar, a stopcock for the introduction of nitrogen, a stopper, and a Dean-Stark trap filled with xylene (about 25 ml). A reflux condenser equipped with a calcium sulfate drying tube was fitted on top of the trap. The flask was purged with nitrogen and charged with N-methyl-pyrollidinone (60 ml), xylene (10 ml), and 1,12-dodecanediamine (2.00 g, 0.0100 mole). Dianhydride (3) (3.34 g, 0.0100 mole) was added to the reagents at one time. The mixture was stirred at room temperature for an hour, at 100° C. for an hour, and then refluxed (about 150° C.) for an additional hour while water was collected in the Dean-Stark trap by azeotropic distillation. The trap was drained and the remaining xylene was distilled from the reaction mixture. After refluxing the NMP solution for two hours, the solution was cooled below 100° C. and poured slowly into water in a rapidly stirring blender. The crude polyimide was isolated as a rubbery solid. It was vacuum dried (250 torr/150° C.) for six hours to yield 4.5 g (91%) of (9) as a clear, slightly yellow, flexible plastic. Anal. Calc'd for $C_{30}H_{46}N_2O_4$: C 72.25, H 9.30, N, 5.62. Found: C 71.17, H 9.38, N 5.57. The inherent viscosity (IV), measured in 60/40 phenol/tetrachloroethane (PTCE), was 0.49 dl/g.

EXAMPLE VIII

Preparation and characterization of polyimide poly(4,4'-oxydiphenylene-3,3'-(1,2-ethandiyl)bis(1,2-dimethylcyclobutane-1,2-dicarboximide)) (10) were as follows:

The same procedure used in Example VII was used to react oxybis(aniline) (2.5 g, 0.0125 mole) with (3) (4.18 g, 0.0125 mole). An off-white powder was isolated 5.95 g (96%) of (10). Anal. Calc'd. for $C_{30}H_{30}N_2O_5$: C 72.27, H 6.07, N 5.62. Found: C 70.30, H 6.19, N 5.86. IV (PTCE) 0.23 dl/g.

EXAMPLE IX

Preparation and characterization of polyimide poly(-dodecamethylene-3,3'-(1,4-butandiyl)bis(1,2-dimethyl-cyclobutane-1,2-dicarboximide)) (11) were as follows:

The same procedure used in Example VII was used to react 1,12-dodecanediamine (2.00 g, 0.0100 mole) with (4) (3.62 g, 0.0100 mole). The polyimide was isolated as a clear, pale yellow, flexible plastic, 3.8 g (72%). Anal. Calc'd. for $C_{32}H_{50}N_2O_4$: C 72.97, H 9.57, N 5.32. Found: C 72.38, H 9.58, N 5.63. IV (PTCE) 0.50 dl/g.

EXAMPLE X

Preparation and characterization of polyimide poly(4,4'-oxydiphenylene-3,3'-(1,4-butandiyl)bis(1,2-dimethylcyclobutane-1,2-dicarboximide)) (12) were as follows:

The same procedure used in Example VII was used to react oxybis(aniline) (2.00 g, 0.0100 mole) with (4) (3.62 g, 0.0100 mole). A white powder was isolated, 4.75 g (90%) of (12). Anal. Calc'd. for $C_{32}H_{34}N_2O_5$: C 72.98, H 6.51, N 5.32. Found: C 71.73, H 6.47, N 5.24. IV (PTCE) 0.23 dl/g.

EXAMPLE XI

Preparation and characterization of polyimide poly(-dodecamethylene-[10.2.0.0.$^{4,7}$]dodecane-5,6,11,12-tetramethyl-5,6,11,12-tetracarboxylic-5:6,11:12-diimide) (13) were as follows:

The same procedure used in Example VII was used to react 1,12-dodecanediamine (3.01 g, 0.015 mole) and dianhydride (5) (5.4 g, 0.015 mole). A white solid was isolated, 6.3 g (80 mole %) of (13). Anal. Calc'd. for $C_{32}H_{48}N_2O_4$: C 73.24, H 9.22, N 5.34. Found: C 70.72, H 9.00, N 5.57. IV (PTCE) 0.27 dl/g.

EXAMPLE XII

Preparation and characterization of polyimide poly(4,4'-oxydiphenylene-[10.2.0.0.$^{4,7}$]dodecane-5,6,11,12-tetramethyl-5,6,11,12-tetracarboxylic-5:6,11:12-diimide (14) were as follows:

The same procedure used in Example VII was used to react oxybis(aniline) (2.40 g, 0.012 mole) and (5) (4.32 g, 0.012 mole). The dry white polyimide (14) was obtained in 88% yield (5.54 g). Anal. Calc'd for $C_{32}H_{32}N_2O_5$: C 73.26, H 6.15, N 5.34. Found: C 67.38, H 6.23, N 4.74. IV (PTCE) 0.14 dl/g.

EXAMPLE XIII

Preparation and characterization of polyimide poly(-dodecamethylene-7,7'-(1,2-ethandiyl)bis(bicyclo[4.2.0]octane-1,6-dicarboximide)) (15) were as follows:

The same procedure used in Example VII was used to react 1,12-dodecanediamine (2.00 g, 0.0100 mole) with dianhydride (6) (4.25 g, 0.0110 mole). A white powder was isolated, 5.87 g (97 mole %) of polyimide (15). Anal. Calc'd. for $C_{34}H_{50}N_2O_6$: C 74.14, H 9.15, N 5.09. Found: C 78.80, H 9.25, N 5.05. IV (PTCE) 0.47 dl/g.

EXAMPLE XIV

Preparation and characterization of polyimide poly(4,4'-oxydiphenylene-7,7'-(1,2-ethandiyl)bis(bicyclo[4.2.0]octane-1,6-dicarboximide)) (16) were as follows:

The same procedure used in Example VII was used to react oxybis(aniline) (2.20 g, 0.0110 mole) with dianhydride (6) (4.25 g, 0.0110 mole). A white powder was isolated, 5.85 g (97 mole %) of polyimide (16). Anal. Calc'd. for $C_{34}H_{54}N_2O_5$: C 74.16, H 6.22, N 5.09. Found: C 72.81, H 6.38, N 5.08. IV (PTCE) 0.20 dl/g.

EXAMPLE XV

Preparation and characterization of polyimide poly(-dodecamethylene-7,7'-(1,4-butandiyl)bis(bicyclo[4.2.0]octane-1,6-dicarboximide)) (17) were as follows:

The same procedure used in Example VII was used to react 1,12-dodecanediamine (2.00 g, 0.0100 mole) with dianhydride (7) (4.15 g, 0.0100 mole). A slightly yellow, flexible plastic was isolated, 4.5 g (78%) of polyimide (17). Anal. Calc'd. for $C_{34}H_{54}N_2O_4$: C 74.70, H 9.40, N 4.84. Found: C 73.82, H 9.36, N 5.56. IV (PTCE) 0.53 dl/g.

EXAMPLE XVI

Preparation and characterization of polyimide poly(4,4'-oxydiphenylene-7,7'-(1,4-butandiyl)bis(bicyclo[4.2.0]octane-1,6-dicarboximide)) (18) were as follows:

The same procedure used in Example VII was used to react oxybis(aniline) (2.00 g, 0.0100 mole) with (7) (4.15 g, 0.0100 mole). A white powder was isolated, 5.50 g (45%) of (18). Anal. Calc'd. for $C_{34}H_{38}N_2O_5$: C 74.72, $H_{6.62}$, N 4.84. Found: C 73.52, H 7.09, N 5.31. IV (PTCE) 0.11 dl/g.

EXAMPLE XVII

Preparation and characterization of polyimide poly(-dodecamethylene-pentacyclo[16.4.0.0$^{2,15}$.0$^{5,12}$.0$^{6,11}$]eicosane-1,6,11,16-tetracarboxylic-1:16,6:11-diimide) (19) were as follows:

The same procedure used in Example VII was used to react 1,12-dodecanediamine (2.40 g, 0.012 mole) and dianhydride (8) (4.95 g, 0.012 mole). A white powder was obtained, 5.79 g (84 mole %) of (19). Anal. Calc'd. for $C_{36}H_{52}N_2O_4$: C 74.9, H 9.09, N 4.86. Found: C 75.01, H 9.23, N 4.99. IV (PTCE) 0.29 dl/g.

EXAMPLE XVIII

Preparation and characterization of polyimide poly(4,4'-oxydiphenylene-pentacyclo[16.4.0.0$^{2,15}$.0$^{5,12}$.0$^{6,11}$]eicosane-1,6,11,16-tetracarboxylic-1:16,6:11-diimide) (20) were as follows:

The procedure of Example VII was used to react oxbis(aniline) (2.40 g, 0.012 mole) with dianhydride (8). A white powder was isolated, 6.59 g (95 mole %) of polyimide (20). Anal. Calc'd. for $C_{36}H_{36}N_2O_5$: C 74.98, H 6.29, N 4.86. Found: C 70.58, H 6.48, N 4.34.

EXAMPLE XIX

Preparation and characterization of copolyimide of poly(dodecamethylene pyromellitic imide) with poly(-dodecamethylene-pentacyclo[16.4.0.0$^{2,15}$0$^{5,12}$0$^{6,11}$]eicosane-1:16,6:11-dicarboximide) (21) were as follows:

The same procedure as in Example VII was used to react 4.80 g (0.024 mole) of 1,12-dodecanediamine with a mixture of 4.95 g (0.012 mole) of dianhydride (8) and 2.62 g (0.012 mole) of pyromellitic anhydride. A white powder was obtained, 11.46 g (95 mole %) of copolyimide (21). Anal. Calc'd. for $C_{58}H_{78}N_4O_8$: C 72.65, H 8.14, N 5.85. Found: C 72.31, H 8.18, N 6.16. IV (PTCE) 0.73 dl/g.

What is claimed is:

1. As a composition of matter a cycloaliphatic tetracarboxylic acid dianhydride of the structure selected from the group consisting of

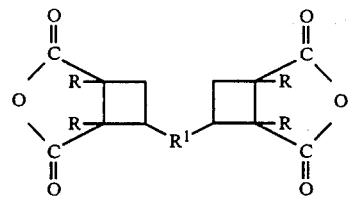

and

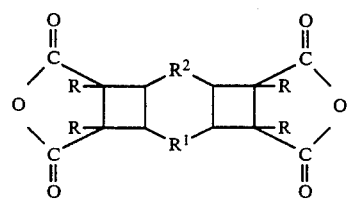

wherein R is selected from the group consisting of alkyl groups of 1 to 10 carbon atoms and alkylene groups of from 2 to 20 carbon atoms linked together to form a ring, and $R^1$ and $R^2$ are individually selected from the group consisting of alkylene groups of from 1 to 10 carbon atoms and aralkylene groups of from 8 to 20 carbon atoms with the provision that hydrocarbon moieties of said groups can contain stable linkages selected from the groups consisting of —O—,

—SO—, —SO$_2$—, and —S— radicals.

2. The composition of claim 1 wherein R is an alkyl group of from 1 to 12 carbon atoms and $R^1$ and $R^2$ are individually selected from the group consisting of alkylene groups of from 2 to 8 carbon atoms.

3. The composition of claim 1 wherein R is a methyl group, and $R^1$ and $R^2$ are alkylene groups of from 1 to 4 carbon atoms.

4. The composition of claim 1 wherein said cycloaliphatic tetracarboxylic acid dianhydride is 3,3'-(1,2-ethandiyl)bis(1,2-dimethylcyclobutane-1,2-dicarboxylic acid dianhydride).

5. The composition of claim 1 wherein said cycloaliphatic tetracarboxylic acid dianhydride is 3,3'-(1,4-butandiyl)bis(1,2-dimethylcyclobutane-1,2-dicarboxylic acid dianhydride).

6. The composition of claim 1 wherein said cycloaliphatic tetracarboxylic acid dianhydride is tricyclo[10.2.0.0$^{4,7}$]dodecane-5,6,11,12-tetramethyl-5,6)11,12-tetracarboxylic acid, 5:6,11:12-dianhydride.

7. The composition of claim 1 wherein said cycloaliphatic tetracarboxylic acid dianhydride is 7,7'-(1,2-ethandiyl)bis(bicyclo[4.2.0]octane-1,6-dicarboxylic acid anhydride).

8. The composition of claim 1 wherein said cycloaliphatic tetracarboxylic acid dianhydride is 7,7'-(1,4-butandiyl)bis(bicyclo[4.2.0]octane-1,6-dicarboxylic acid anhydride).

9. As a composition of matter, a cycloaliphatic tetracarboxylic acid dianhydride of the structure

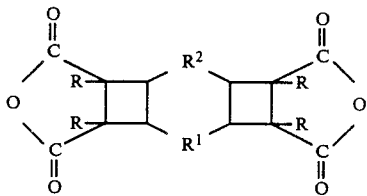

wherein R is an alkylene group of from 2 to 20 carbon atoms linked together to form a ring, and $R^1$ and $R^2$ are individually selected from the group consisting of alkylene groups of from 1 to 10 carbon atoms and aralkylene groups of from 8 to 20 carbon atoms with the provision that hydrocarbon moieties of said groups can contain stable linkages selected from the groups consisting of —O—,

—SO—, —SO$_2$—, and —S— radicals.

10. The composition of claim 9 wherein R, $R^1$ and $R^2$ are alkylene groups of 2 to 4 carbon atoms.

11. The composition of claim 10 wherein said cycloaliphatic tetracarboxylic acid dianhydride is pentacyclo[16.4.0.0$^{2,15}$.0$^{5,12}$.0$^{6,11}$]eicosane-1,6,11,16-tetracarboxylic acid, 1:16,6,11-dianhydride.

12. As a composition of matter, a cycloaliphatic tetracarboxylic acid dianhydride prepared by photocycloaddition of a maleic anhydride compound of the structural formula

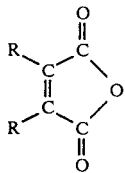

wherein R is individually selected from the group consisting of alkyl moieties of from 1 to 10 carbon atoms and alkylene moieties of from 2 to 20 carbon atoms linked together to form a ring, to at least one diolefin selected from the group consisting of alpha-, omega-linear diolefins of 4 to 100 carbon atoms and cyclic diolefins of the structure

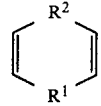

wherein $R^1$ and $R^2$ are individually selected from the group consisting of alkylene groups of from 1 to 100 carbon atoms and aralkylene groups of from 8 to 20 carbon atoms with the provision that hydrocarbon moieties of said diolefins can contain stable linkages selected from the group consisting of —O—,

—SO—, —SO$_2$—, and —S— radicals in the presence of an ultra-violet light sensitizer using actinic radiation as an energy source at a temperature from about $-10°$ C. to about 150° C.

13. The composition of claim 12 wherein said maleic anhydride compound is dimethyl maleic anhydride.

14. The composition of claim 12 wherein said maleic anhydride compound is 1-cyclohexene-1,2-dicarboxylic acid anhydride.

15. The composition of claim 12 wherein said hydrocarbon moiety of said alpha-, omega-linear diolefin contains from 4 to 12 carbon atoms.

16. The composition of claim 12 wherein said $R^1$ and $R^2$ are individually selected from the group consisting of alkylene groups of from 2 to 8 carbon atoms.

17. The composition of claim 12 wherein said diolefin is 1,5-hexadiene.

18. The composition of claim 12 wherein said diolefin is 1,5-cyclooctadiene.

19. The composition of claim 12 wherein said diolefin is 1,7-octadiene.

* * * * *

UNITED STATES PATENT OFFICE
CERTIFICATE OF CORRECTION

Patent No. 4,490,545        Dated December 25, 1984

Inventor(s) Winzenburg, Mark L.-Fields, Ellis K.-Shneider, Benjamin

It is certified that error appears in the above-identified patent and that said Letters Patent are hereby corrected as shown below:

Column 13, line 26, "$H_{6.62}$" should be -- H 6.62 --.

Column 13, lines 31-32, "$.0^{6,1-}1]$" should be -- $.0^{6,11}]$ --.

Column 15, line 29, "1:16, 6, 11" should be -- 1:16, 6:11 --.

Signed and Sealed this

Fifteenth Day of October 1985

[SEAL]

Attest:

Attesting Officer

DONALD J. QUIGG

Commissioner of Patents and
Trademarks—Designate